United States Patent
Lütz et al.

(10) Patent No.: US 10,420,912 B2
(45) Date of Patent: Sep. 24, 2019

(54) SYSTEM FOR INFLUENCING THE SENSES OF A PERSON AND ROOM EQUIPMENT HAVING SUCH A SYSTEM

(71) Applicant: Graft Gesellschaft von Architekten mbH, Berlin (DE)

(72) Inventors: Alawi Lütz, Berlin (DE); Claudia Spies, Berlin (DE); Thomas Willemeit, Berlin (DE); Annette Finke, Berlin (DE)

(73) Assignee: Graft Gesellschaft von Architekten mbH, Berlin (DE)

( * ) Notice: Subject to any disclaimer, the term of this patent is extended or adjusted under 35 U.S.C. 154(b) by 206 days.

(21) Appl. No.: 15/500,639

(22) PCT Filed: Jul. 31, 2015

(86) PCT No.: PCT/EP2015/067731
§ 371 (c)(1),
(2) Date: Jan. 31, 2017

(87) PCT Pub. No.: WO2016/016455
PCT Pub. Date: Feb. 4, 2016

(65) Prior Publication Data
US 2017/0224950 A1    Aug. 10, 2017

(30) Foreign Application Priority Data
Aug. 1, 2014   (DE) .................. 10 2014 215 212

(51) Int. Cl.
*A61M 21/00* (2006.01)
*H04N 9/31* (2006.01)
(Continued)

(52) U.S. Cl.
CPC ............. *A61M 21/00* (2013.01); *A61G 10/00* (2013.01); *E04B 1/8209* (2013.01); *E04B 1/86* (2013.01);
(Continued)

(58) Field of Classification Search
CPC ......... A61M 21/0094; A61M 2021/0044–005; A61M 21/02; F21W 2131/20–208;
(Continued)

(56) References Cited

U.S. PATENT DOCUMENTS 3,822,693 A   7/1974 King
4,109,331 A   8/1978 Champeau
(Continued)

FOREIGN PATENT DOCUMENTS

DE   2648442 A1   5/1977
DE   10232889 A1   1/2004
(Continued)

*Primary Examiner* — Catherine B Kuhlman
(74) *Attorney, Agent, or Firm* — The Webb Law Firm

(57) ABSTRACT

A system for influencing the senses of a person in a room for measuring and/or influencing physiological parameters of the person is provided. The person is substantially stationary and lying in the room during the measurement and/or influencing. The system includes a sound insulating apparatus for screening off acoustically active devices with respect to the person. The acoustically active devices serve for measuring and/or influencing the physiological parameters in the room, and an optical display apparatus for offering optical stimuli and/or signals for the person in the field of view of the person.

21 Claims, 7 Drawing Sheets

(51) Int. Cl.
*E04H 3/08* (2006.01)
*A61G 10/00* (2006.01)
*E04B 1/82* (2006.01)
*E04B 1/86* (2006.01)
*E04B 9/30* (2006.01)

(52) U.S. Cl.
CPC ............... *E04H 3/08* (2013.01); *H04N 9/31* (2013.01); *A61M 2021/0027* (2013.01); *A61M 2021/0044* (2013.01); *A61M 2205/42* (2013.01); *E04B 9/303* (2013.01)

(58) Field of Classification Search
CPC ...... G04G 9/0052; H04N 9/3155; H04N 5/74; H04N 5/7475; H04N 9/04555; H04N 9/3164; F21V 9/02; F21V 33/0068–0072; G03B 21/26
See application file for complete search history.

(56) References Cited

U.S. PATENT DOCUMENTS

| | | | | |
|---|---|---|---|---|
| 5,676,633 | A | * | 10/1997 | August ................ A47C 21/00 600/26 |
| 7,766,503 | B2 | * | 8/2010 | Heiking ................ F21S 8/026 362/147 |
| 2002/0198438 | A1 | * | 12/2002 | Cromer ................ A61M 21/02 600/27 |
| 2006/0030907 | A1 | | 2/2006 | McNew |
| 2008/0243211 | A1 | | 10/2008 | Cartwright et al. |
| 2009/0180077 | A1 | * | 7/2009 | De Vaan ................ G03B 21/62 353/30 |

FOREIGN PATENT DOCUMENTS

| | | |
|---|---|---|
| EP | 2375151 A2 | 10/2011 |
| JP | 2007294143 A | 11/2007 |

\* cited by examiner

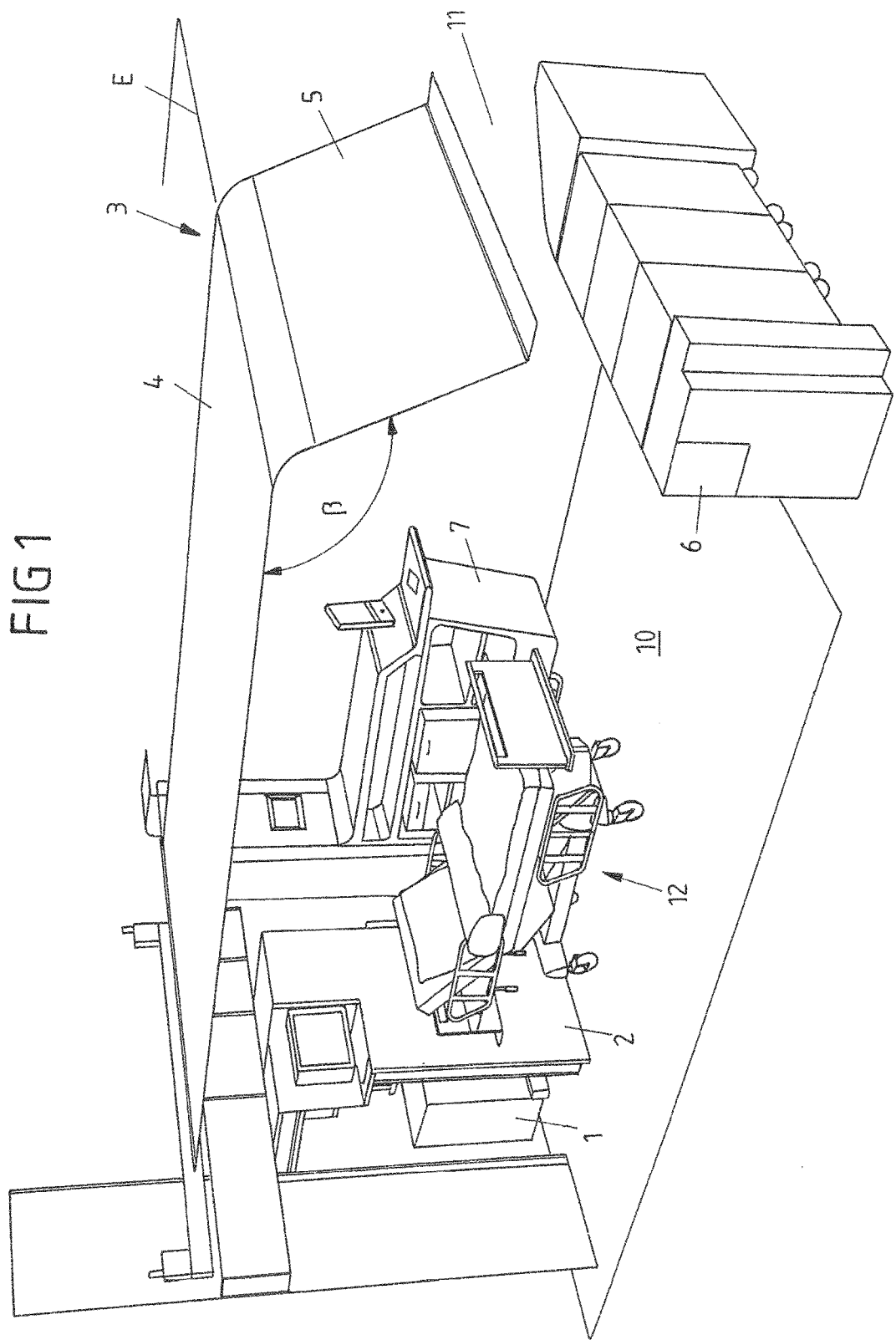

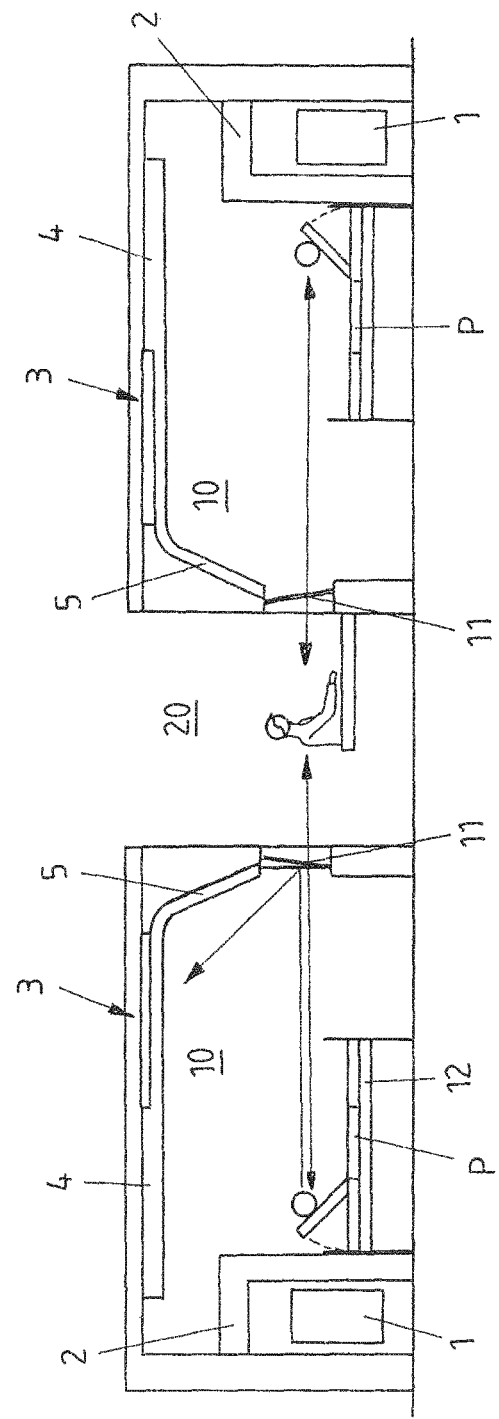

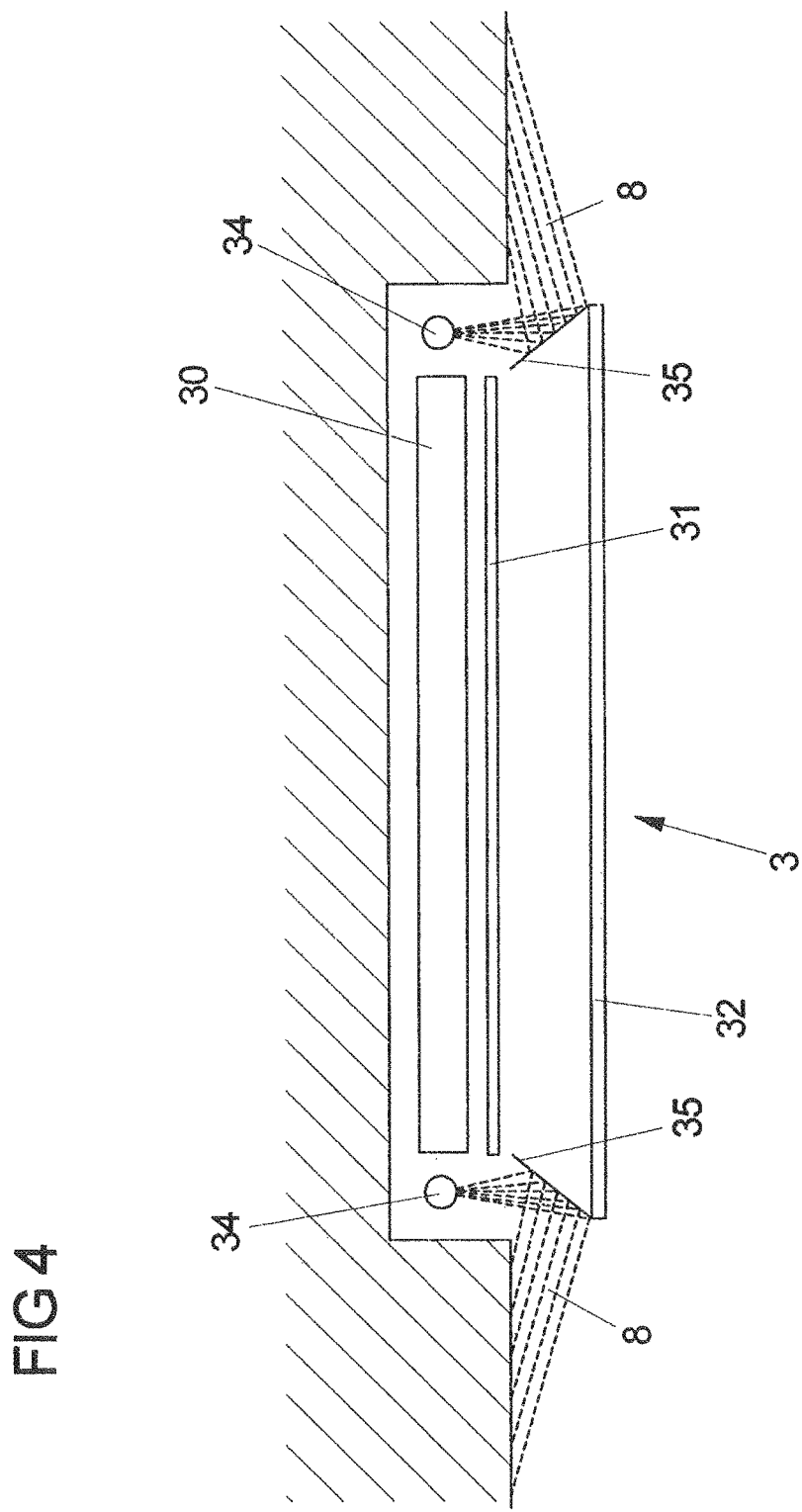

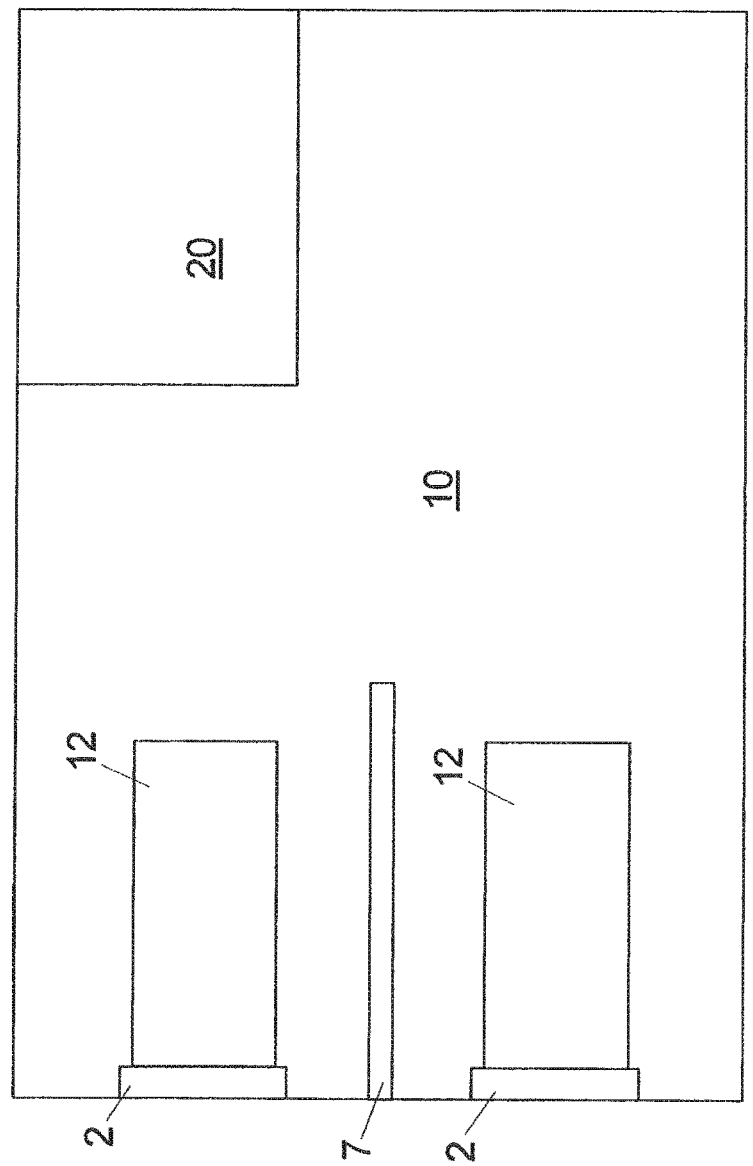

SYSTEM FOR INFLUENCING THE SENSES OF A PERSON AND ROOM EQUIPMENT HAVING SUCH A SYSTEM

CROSS-REFERENCE TO RELATED APPLICATIONS

This application is the United States national phase of International Application No. PCT/EP2015/067731 filed Jul. 31, 2015, and claims priority to German Patent Application No. 10 2014 215 212.7 filed Aug. 1, 2014, the disclosures of which are hereby incorporated in their entirety by reference.

BACKGROUND OF THE INVENTION

The invention relates to a system for measuring the effect of sensory perception within a defined space and furthermore for influencing the senses of a person within such a space and to room setup having such a system.

Simulating influences influence physical well-being in many respects. Capturing specific effects of stimuli and/or achieving specific stimulating effects is difficult, since people are subject to many different non-specific stimuli.

SUMMARY OF THE INVENTION

An object is therefore to effect the influencing of the senses in a defined form.

The object is achieved by way of a system having features as described herein.

A sound insulation apparatus here serves for shielding of acoustically active devices with respect to a person, wherein the acoustically active devices are used for measuring and/or influencing the physiological parameters within the room. The person is here in a stationary position, i.e. he or she does not move freely within the room.

Additionally, an optical display device serves for offering optical stimuli and/or signals for the person within the field of view of the stationary person, wherein the optical display apparatus extends in at least one viewing direction of the stationary lying person over a viewing angle of at least 40° and at most 180°, in particular between 55° and 75°, very particularly of 70°, wherein the viewing angle α extends in a plane that extends downward from the viewing direction or to the left and to the right from the viewing direction. It is the combination of an active optical display apparatus in a specific arrangement directed to the person with a sound insulating apparatus that makes it possible to measure and/or influence the well-being of the person in a targeted manner.

It may be advantageous here if the inclination of the stationary lying person in the head region is between 0° and 65°, in particular between 0° and 45°. Specifically in the environment of an intensive care unit, the acoustically active devices have at least one infusion pump, at least one suction apparatus, a dialysis apparatus, a ventilator and/or a hemodynamic monitor.

It is particularly advantageous here to arrange the sound insulating apparatus behind the head region of the stationary lying person, since effective sound guidance is achieved in this way without adversely affecting the functionality of the shielded devices. In one advantageous embodiment of the system, in particular the sound insulating apparatus reduces the average sound emission of the active acoustic devices within the room to at most 55 dB(A), in particular at most 40 dB(A), measured on the person within the room. Further sound-damping measures can be added, if appropriate, such as the realization of a sound-damping floor, sound-damping walls and ceilings, and/or sound-damping areas within the room.

One advantageous embodiment of the system furthermore has a sound insulating apparatus having a means for absorbing and damping sound that is emitted within the sound insulating apparatus and/or directed from the room into the sound insulating apparatus.

For comprehensive optical influencing of the person, it is advantageous if the optical display apparatus extends in the use of the stationary lying person to the rear beyond the head position.

It is possible to achieve efficient adaptation to a room, in particular an intensive care room, if the optical display apparatus has at least two display areas which are oriented differently in terms of space or a display area which is curved, wherein the optical display apparatus is arranged at least partially above the stationary lying person in a plane that is oriented in particular substantially parallel to the lying position of the person. It is thus possible to offer optical stimuli for the person on a contiguous area.

What is particularly advantageous when adapting to a room is if a second display area of the optical display apparatus is arranged in the viewing direction of the person at an angle β of between 90° and 160°, in particular at an angle β of between 110° and 120°, and very particularly at an angle β of 114°, wherein the angle β is measured from a plane that extends above and parallel to the stationary lying person. The person can thus also perceive optical stimuli in a half-sitting position.

The transition region between the first display area of the optical display apparatus and the second display area of the optical display apparatus advantageously has a rounded design, in particular having a radius of curvature of between 20 and 40 cm. Consequently, the person perceives the two display areas substantially as a single surface.

In a further embodiment, the optical stimuli and/or signals that originate from the optical display apparatus comprise information representations, task lighting and/or biodynamic lighting. By integrating the provision of stimuli and illumination, a space-saving construction can be achieved and at the same time an efficient way of controlling it. On account of this configuration, the optical display apparatus additionally has an integration in an area such that the perception is one of an architecturally effective room surface, as a frame-less room surface, as an illuminating ceiling and/or wall, rather than as a device.

Is advantageous here if a first luminous means, in particular a luminous field having LEDs or OLEDs, is used for functional illumination, task lighting and/or biodynamic lighting of the room within the region of the person, and a second luminous means, which is controllable independently of the first luminous means, in particular an LED grid or an OLED apparatus, is used for the display of patterns or optical stimuli, in particular as an entertainment light or for display with visual content. Due to the independent control, it is possible for example for a circadian illumination to be effected by way of the first luminous means, wherein independently thereof, color patterns or images can be displayed by way of the second luminous means.

What is particularly advantageous is if the superposed optical signals of the two luminous means are incident on a translucent projection area that is located within the field of view of the person.

To provide the optical stimuli across large areas, it is advantageous if a view cone about the viewing direction of the stationary lying person has an opening angle of at least 40° and at most 180°, in particular between 55° and 75°, very particularly of 70°.

In one advantageous embodiment, it is also possible to use the optical display apparatus to display optical stimuli and/or signals for the stationary lying person, wherein the stimuli and/or signals are preprogrammed and/or controllable by way of data measured on the person. In the case of a preprogrammed control, it is possible for example for specific daytime patterns to be taken into account. These optical stimuli can be coupled to reactions in a person by way of alternative or combined feedback from the person.

For further sound damping it is advantageous if the optical display apparatus has sound absorbing materials.

To delimit the thermal load of the room, the optical display apparatus has a cooling load of less than 2000 W, in particular less than 1500 W.

A particularly advantageous effect occurs if the peripheral region of the optical display apparatus has at least partially indirect ceiling illumination. Additionally or alternatively, the optical display apparatus can be a seamless ceiling element.

The object is also achieved by way of room setup having a system for influencing the senses of a person, having features as described herein. Sound-damping materials in at least part of the floor, the walls and/or the ceiling of the room here serve for creating an environment that is pleasant for the person.

It is advantageous if at least two systems as described herein are provided, wherein in each case a sound insulating barrier, in particular in the form of a visual protection barrier, is arranged between two stationary lying people, wherein the sound insulating barrier has in particular at least partially a surface with a wood structure. The wood structure constitutes a positive visual stimulus for the person.

In this way, persons are not disturbed by one another. To create a private area, which is important in particular in the environment of an intensive care unit, the sound insulating barrier on the side of the person has an apparatus for attaching information carriers, on which for example personal objects, such as photos or images, can be arranged.

It is also advantageous if the sound insulating barrier has a means for absorbing and damping sound that is emitted in the interior of the sound insulating barrier and/or enters it from the room.

It is necessary especially in the area of an intensive care unit for the person to be regularly monitored. In order to minimize the influences caused by this monitoring, one embodiment of the room setup has at least one observation window for observers outside the room, wherein the at least one observation window is inclined with respect to the wall of the room by 5 to 10°, in particular 8°, to avoid reflected images of the lying stationary person.

Room setup can include two opposite rooms which are connected via an interconnected observation room having at least two observation windows, such that observation of two rooms from the observation room is made possible. It is particularly advantageous here if at least two observation windows for observers outside the observation room are fitted with a polarization apparatus. Due to appropriate arrangement of the polarization angle, clear view through can be avoided. In particular, the polarization film can be arranged in each case such that a view through two observation panes which are located one behind the other is avoided by way of the light transmittance through both observation panes being less than 98%.

Advantageously, the system of the room setup is adapted and configured for a person lying in intensive care and/or a wellness region. With the targeted optical and acoustic influencing, it is possible for example for the effects of jetlag of a person to be alleviated by biodynamic light.

A further advantageous embodiment of the room setup has light control of the room, having the following light parameters:
light intensity during the day: 300 lx (in the morning), 1700 lx (noon) and 100 lx (in the evening),
light intensity at night: <3 lx,
light color: 2700-6500 K over the course of the day matched to the natural progression,
light temperature infinitely variable in different scenarios with different percentage proportions, and/or
luminance <500 cd m$^{-2}$.
The reference variable for the light intensities is 110 cm horizontally above the floor of the room.

In one alternative embodiment, the following target variables are used (reference variable 110 cm horizontally above the floor of the room):
maximum light intensity between 1800 and 2800 lx, in particular 1800 and 2400 lx, very particularly between 1800 and 2100 lx,
light color: between 2700 and 6500 K, in particular between 3000 and 5000 K.

In particular, it is advantageous if at least one light parameter is time-controlled, in particular adaptable to the progression over the day.

A further advantageous embodiment of the room setup has a sound insulating room having at least one workstation for care providers, an alarm station for giving off acoustic alarms (alarm transmission from the room), a glass discarding apparatus, a linen storage means and/or a pharmaceutical storage means.

The room atmosphere is also positively influenced if the wall at the back of the stationary lying person and/or the floor of the room has a low-light-reflection surface.

BRIEF DESCRIPTION OF THE DRAWINGS

Embodiments of the invention are illustrated by way of example with reference to images.

FIG. 1 shows a schematic illustration of an embodiment of a room setup having a system for influencing a lying person in a room of an intensive care unit;

FIG. 1A shows a detailed drawing with an inclined observation window in the wall of the room according to FIG. 1;

FIG. 4 shows a sectional view of an embodiment of an optical display apparatus;

FIG. 7 shows a room plan with embodiments of a system for influencing the senses of a person in an intensive care unit.

DETAILED DESCRIPTION

Figure 3:
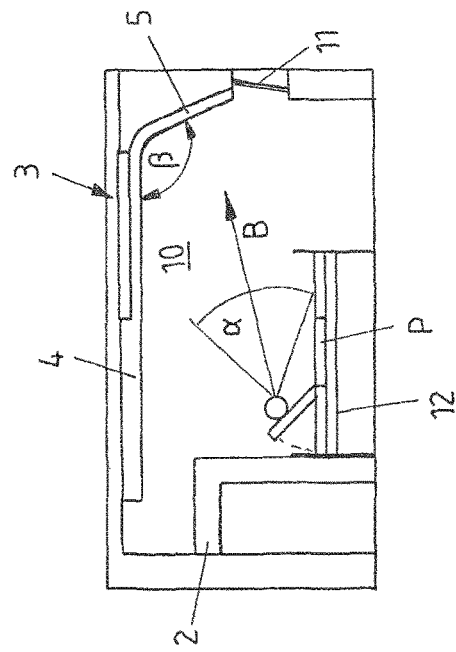
FIG. 3 shows a view of an embodiment of the system for influencing a lying person, wherein the person is lying while having an inclined head region.

Embodiments of the system for influencing a stationary lying person P by way of one or more rooms 10 of an intensive care unit (see for example FIG. 1, FIGS. 1A and 7) is illustrated below. However, it is also possible in principle to use the embodiments in research for capturing human reactions or in a wellness region for relaxation. A typical application can be the therapy of the negative effects of jetlag.

In the case of the intensive care unit, the person P is assumed to be stationary and lying, i.e. the person P is lying in particular in a bed 12, while being able in principle to move therein, for example the person P can turn onto his or her side. It is likewise possible to incline the head region of the person P with respect to the horizontal (i.e. the plane of the bed). However, the person P does not freely move within a room 10.

The stationary, lying position of the person P permits alignment and configuration of specific means for influencing the senses of the person P, which will be explained in more detail below. Here, optical and acoustic stimuli are combined and influenced in a targeted fashion. Initially, general principles of the system illustrated here and the room setup having the system will be described, and subsequently embodiments of the system and the room setup will be described with reference to figures.

For example, the perception from the perspective of a critically ill person P can be examined using such a system and room setup with the objective of documenting, in the specific exceptional situation of residence in an intensive care unit, a significant reduction of stress symptoms for improving the health situation generally and for decreasing the delirium rate specifically.

Treatment environments to date of persons P which are bound to intensive care influence the visual, acoustic perception, the spatial and temporal orientation due to a large number of influencing factors. In particular, phenomena of hopelessness all the way to panic can be identified, in particular as fear and stress factors, which have an effect on the persons P. Praxis to date of increased administration of pain medication, for example for sedating the persons P, not only results in an identifiable delayed healing process, but in particular also an increased delirium rate.

Improvement of the environment of the persons P appears desirable. Here, the room setup and in particular the effect of everyone on the perception of health of the patients to be treated are to be improved in a sense such that the environment has a fear and stress reducing effect, such that administration of pain medication and sedation can be reduced and healing progressions are promoted in an optimized fashion and the delirium rate can be reduced.

By way of a targeted replacement of the lack of daylight, by influencing the day and night cycles and/or minimizing negative effects due to increased noise pollution, the persons P can be influenced by the system in a targeted fashion and the effects on the person P can simultaneously be captured.

Comprehensive examination of the perception that is in effect at the same time has hitherto not always been possible in an intensive care environment, since the conventional room architecture is largely limited to meeting functional criteria of the necessary medical treatment and neglects perception phenomena from the view of the patient, which are powerful in terms of their influence. For optimized viewing and observation of such perception phenomena and possible influencing thereof for promoting the healing progression, room and media architectures have been developed using the system illustrated here for influencing the person P.

In order to investigate these phenomena in their entirety, in one embodiment a trial setup is described which takes into account individual factors and can influence them. The trial setup can be used in the same or modified form in real intensive care units.

The embodiments are based on the typical arrangements and requirements of an intensive care medical room 10. Furthermore, a room configuration independent of care and nursing has been developed which integrates the acoustic and visual perception parameters such that the healing progression may be influenced in a positive manner and occurrence of symptoms connected to fear and stress is minimized.

Important influence parameters are in particular the room acoustics, noise, traffic in the intensive care unit, subjective feeling of helplessness and dependence, subjective feeling with respect to the room temperature, temporal and spatial orientation, and in particular also visual stimuli or a lack of stimuli in the region of the view cone of the stationary lying person P.

These influencing parameters influence the occurrence of fear, stress, subjective sensation of pain, and furthermore an inhibited healing progression and the increasingly diagnosed occurrence of delirium and hallucinations.

Since these pathologies are important not only as a diagnosis limitation, but can in particular slow, inhibit or entirely prevent a healing progression in the post-operative exceptional state, all provably identifiable influencing factors are particularly relevant. The system for influencing the senses of the person P can serve among others for identifying details of the influencing parameters, specifying them and developing strategies, if appropriate, relating to how they can be addressed. However, the system can also be used in regular therapy in intensive care units or regular hospital wards.

In addition to the necessary medical care in intensive care units, a system is described with which observation of persons P can be carried out.

Concentrating on what the person P hears and sees is the starting point for a paradigm shift in intensive medical architecture away from functional technical construction with apparatus and supply lines, which are necessary within the framework of medical care, toward an "experienced" scenography that is describable from the view of the patient. It is intended to render the subjective feeling of the patient positively influenceable in a predictable manner, as viewed from the medical standpoint, and to thus have a measurable effect on the healing progression of the patient. Lowering stress by way of reducing stress factors and the construction as a perception machine for patients, which can be used to distract, relax or entertain, leads to the thesis of an actual influenceability of the physical state by way of a room configuration and architecture in the novel trial setup.

For the stationary lying person P, the field of vision of the person P is definable relatively exactly within the framework of the intensive care unit. It is possible to carry out not only surveys but also measurements in a controlled manner and to establish a comparability in the observation of various persons P. Moreover, in the exceptional state of a post-operative stationary residence, the influencing factors of generally incidental influences such as lack of daylight, restlessness during sleep, unaccustomed acoustics and environment, unknown environment, and risk of disorientation seem to have a specific influence on the healing progression, which however in this case is at the forefront of every medical consideration. Moreover, this also permits the assumption that it is possible, within the framework of perception and delirium research, for findings relating to the effect of rooms and room environments to be generally derived.

Patients in intensive care units regularly suffer disturbances of the sleep/wake cycle, which are accompanied by a poor quality of sleep. Light is the most important time indicator for maintaining the physiological day/night cycle in humans. This cycle is controlled by the epiphyseal hormone melatonin. Disturbances of the day/night cycle are therefore generally characterized by a dysregulation of the physiological profile of melatonin release. The secretion of the epiphyseal hormone melatonin, which is synthesized from the biogenic amino acid tryptophan, is dependent on light exposition. In addition to the disease itself and the medicaments which the patient receives during his or her treatment in the intensive care unit, inadequate light conditions in the treatment rooms can also trigger or promote sleep disturbances, which consequently also cause organ dysfunctions of the brain and therefore have an effect that is not only acute but also negative in the long run with respect to the treatment result of the patient.

Within the framework of the embodiments illustrated here, the matter at hand relates to the creation of a room atmosphere which
- removes the fear of the treated patient in the room, as a result of which sedatives can be saved, which could subsequently have a positive influence on the general healing progression of the patient.
- offers orientation aids with respect to the time of day for the treated patient in the room, as a result of which acute deliriums and states of confusion of patients can be reduced, which could subsequently have a positive influence on the general healing progression of the patients.
- optimizes work processes for the staff such that more effective and time-efficient secure work is possible, while at the same time also supporting the remaining objectives, which are defined here.

For developing the room trial setup, initially the individual influencing parameters are identified, which ascertain and influence the perception of the person P.

Acoustic Perception

Proceeding from the spatial positioning of the person P in the room 10, information relating to existing sound sources is initially recorded and optimized with respect to the defined target variables. Defined target variables for embodiments of the system are as follows:
- day: noise reduction: noise level <55 dB(A)
- night: noise reduction: noise level <40 dB(A)
- avoid peak level >85 dB(A)
- avoid continuous (>30 min) peak levels >70 dB(A)

These values—and all comparable values below—are to be understood as being temporal and/or spatial averages.

Owing to the embodiments illustrated here, the average sound levels in the treatment rooms can be reduced by up to 6 dB, which corresponds to a volume reduction to 0.66 times the original value. In addition, it was possible to reduce the proportion of maximum sound levels from >60 dB at night in the treatment rooms by more than half (27-30%). In the process, it was possible to reduce in particular the frequency of night-time sound level peaks caused by care providers in the treatment rooms. The observation room 20, which in one embodiment is provided between the two rooms, appears to play a decisive role here.

In one embodiment, in each case two loudspeakers are provided at identical distances from the ears of a lying person.

Figure 6:
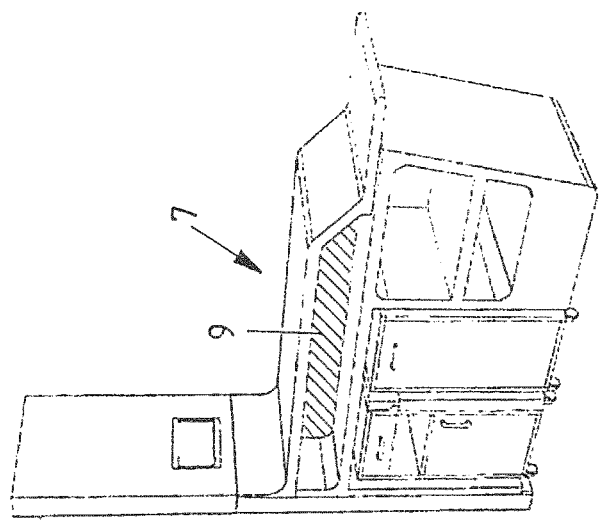
FIG. 6 shows a view of an embodiment of a sound insulating barrier.

This can be achieved for example in a simple manner by mounting the loudspeakers to the right and to the left of the person P in sound insulating barriers, as are illustrated for example in FIG. 6.

Due to the symmetric emission of sound, a calming effect is achieved. The loudspeakers have a corresponding directional characteristic for emitting sound into the defined patient zone and avoiding diffused sound (protection of the neighboring patient).

In one embodiment, an individual controller can be provided here, which results in calming and cognitive stimulation of the person P. The realization in individual rooms permits, in one particular embodiment, the examination of the (calming) effect of various sound-emission patterns.

An apparatus for active noise compensation may also be provided, in which noisy undesired sound is canceled by way of destructive interference or at least is rendered more bearable.

With the aid of loudspeakers and using a soundscape, a health-promoting room atmosphere can be generated, which provides a calming, individually adaptable and thus familiar environment by way of acoustic superposition of the given environment sounds. Sound sources with a noise characteristic with negative connotation (noise of ventilator) can thus be perceived as being less evident.

Visual Perception

Optimization of the light conditions on the intensive care unit improves the quality of sleep of the persons P, with significantly less pain medication needing to be applied and fewer depressive symptoms occurring.

Important parameters of the illumination are here glare, light intensity, light color and/or temporal sequence of these parameters through the day. Defined target variables are here (reference variable 110 cm horizontally above the floor of the room (10)):
- light intensity during the day (300 lx in the beginning (morning), 1700 lx (noon) and/or 100 lx in the evening, i.e. circadian (biodynamic) light control is present.
- light intensity during the night <3 lx.
- light color: 2700-6500 K through the day adapted to the natural changes.
- light temperature infinitely variable in various scenarios with different percentage proportions.
- glare behavior, luminance to be kept as low as possible, utilize full illumination area. <500 cd m$^{-2}$.

In one alternative embodiment, the following target variables are used (reference variable 110 cm horizontally above the floor of the room (10)):
- maximum light intensity between 1800 and 2800 lx, in particular 1800 and 2400 lx, very particularly between 1800 and 2100 lx,
- light color: between 2700 and 6500 K, in particular between 3000 and 5000 K.

Here, the light intensities are greater then the threshold necessary for melatonin suppression. Technical capabilities of automated adaptation of the light color temperature also become daytime rhythmization of the patients. Here, sufficient illumination intensity with simultaneous maintenance of the absolute glare tolerance of 10,000 cd/m$^2$ especially with maximum illumination intensity in the viewing direction of the person (P) toward the luminous means is present.

It is possible especially using embodiments of the invention, to carry out examinations in a targeted fashion to ascertain specific parameter combinations. The embodiments are here sufficiently flexible to allow corresponding target variables to be set retroactively and for sufficient illumination intensities to be achieved.

It is also possible to ascertain, using the embodiments, how large the light intensity must be for it to exceed the threshold necessary for melatonin suppression and which exposure duration to the greatest light intensity is expedient for the described effects. The light intensities used through the day reach, as a daily average, glare values of 400 to 600 $cd/m^2$, in particular around 500 $cd/m^2$. Averaging is here carried out for example over the field of vision of the person (P) and over time.

If one of the embodiments is used for research purposes, the following measures can be taken, for example:

Sleep stage determination using electroencephalography (polysomnography).

Determinations of melatonin, cortisol and specific clock genes (molecular genetic measurements) in the blood for imaging (disturbances) of the circadian rhythm.

Performance of the planned cognitive batteries of tests and questionnaires relating to the quality of life and post-traumatic stress disorder within the framework of a follow-up, 3 and 6 months after release from the intensive care unit.

On account of the supplementations and adaptations of the original study protocol which are outlined here, it is ultimately possible to make a much more differentiated scientific statement relating to the effectiveness of the developed innovations.

The acoustic and visual stimuli have a specific meaning. In addition, there exists a series of further influencing variables.

Room Climate

Defined target variables are here:

optimization of ventilation flow to the position of the person P optimization of air filter configuration of germ-free environment use of warm materials, such as for example wood materials.

Measures will be described below, which are used, individually or in combination, to improve the environment of the person P.

Measures Relating to the Acoustics

Acoustically concealing the acoustic active medical devices 1 from the person P by way of a sound insulating apparatus 2, in particular a rear wall behind the person P. Here, sounds of the acoustic active medical devices 1, such as for example beeps, alarm signals of the infusors, sounds of monitoring monitors, ventilators or dialysis machines of patients are dampened. Due to the positioning for example of the ventilator or of the infusors behind the sound insulating apparatus (or in the acoustic shadow) at the head end of the bed 12, the person P is not located in the field of the direct sound. In particular, a trilateral encasement can screen off the direct introduction of noise with respect to the person P. Other small medical devices, such as for example suction devices, gas connections and other connections, can be arranged laterally or behind the sound insulating apparatus 2 at the head end of the bed 12, with the result that the person P is not located within the field of the direct sound of these devices 2. The influx of sound that occurs through work at the connections or devices 2 is also minimized.

By spatially positioning a work plane in the acoustically screened-off region approximately 30 cm to 90 cm behind the lying person P, a low disturbance of the person P on account of work operations by the care providers is achieved.

By positioning a sound insulating barrier 7 between two beds 12 at a height of, for example, 120 cm in the region of the head end of the bed 12, direct sound is screened off. Protrusions and recesses in the sound insulating barrier assume the function of scattering direct sound and thus keeping contents of conversations incomprehensible for neighboring patients. In addition, a private plane is created at eye level of the person P for the purposes of positive superposition/distraction.

Noise from the ventilation is dampened.

Avoidance of work noise and conversation by the care providers at the patient bed, at the neighboring patient and through the corridor.

Avoidance of reverberating surfaces of the furniture. Reduction in the surrounding noise level due to care providers on account of adapted room layout with an observation room 20 which is arranged centrally (indirect patient monitoring). As opposed to a known patient room, in which all work by the care providers is carried out within the room 10, the spatial structure is modified such that a closed observation space 20 is created between two patient rooms 10, in which work such as documentation, material refills, diagnosis, discussion relating to the doctor's rounds etc. can be carried out. The alarms of the medical devices are also connected in the observation room 20, such that they do not occur in a disturbing manner in the patient room 10. As a result, alarm noises, work noises, additional noises caused by the care providers, such as conversation etc., are acoustically removed.

Further reduction of the alarm noises with connected alarms in the observation room 20.

Reduction in the environment noise level by use of self-closing door systems.

Lowering the sound level and the reverberation time in the room 10 by using sound-dampening materials in the ceiling region and use of sound-absorbing covering of the ceiling elements, including at least partially of the optical display apparatus 3.

Reduction of the work noise level by mobile furniture.

Reduction of the perceived noises from the neighboring patient by way of sound insulating barrier 7 between the two beds 12.

Reduction of the noise level by using wood materials or mineral material plates as opposed to stainless steel materials. (door or drawer noises/oscillating behavior/low frequency range).

Use of heavy wood material plates and mineral material plates for sound-proofing.

Measures Relating to the Visual Perception

Configuring the visible surface of the room 10 as a spatially controlled figure permits control of the visual perception of the person P for example by way of a programmable image plane and/or imaging elements on the surface of an optical display apparatus 3. Taking into account the actual field of vision of the stationary lying person P, it is possible here to use as the central unit a large-format ceiling element as an optical display apparatus 3, with which visual contents can be displayed in a controlled manner, but optimized illumination elements can also be integrated.

As is illustrated below, the arrangement of the optical display apparatus 3 can be effected not only on horizontal parts of the ceiling.

The use of natural surfaces/wood grains not only has an acoustic effect, but also a visual effect.

A few features of the optical display apparatus 3 will be listed below, which can be used individually or in combination:

Superposition of controllable illumination elements with a second luminous means 31, in particular an LED grid, for the controlled display of optical patterns or contents for the person P.

Programming the progression of light intensity and color as a function of time of day and/or seasonal classification.

Optimized installation of the luminous means 30, 31 with respect to the viewing angle or the field of vision of the person P.

Integrating more than one illumination function in the optical display apparatus 3, in particular the first luminous means 30: basic illumination, circadian light, biodynamic light, and task light.

Layered construction of the optical display apparatus 3 with different luminous means 30, 31 for the functions biodynamic light/function light/task light/ambient light in a seamless area as an integral room component.

The optical display apparatus 3 which is mounted over a large area over the beds 12 has a sound-absorbing covering 32, which also forms a projection area.

Each individual bed 12 is acoustically surrounded by a laterally flanking sound insulating barrier 7, the rear-side sound insulating apparatus 2 and the optical display apparatus 3, which extends down to 150 cm also on the opposite bed wall. That means that the optical display apparatus 3 interacts in particular with the sound insulating apparatus 2 for providing a defined environment for the person P.

Reducing the glare sensation by warm white LEDs in coves laterally of the optical display apparatus 3.

The room perception of the real room 10 and the surfaces of the optical display apparatus 3 on which media play form complementary poles of an atmospheric and scenographic concept, which serves for perception research under the effect of light, noise and temperature.

Room-related stress factors of an optical type are intended to be reduced measurably. For optimum effect of the optical display apparatus 3 and its scenography, it is necessary to rule out or at least reduce a series of ever-present disturbance factors in the intensive care room, i.e. in the room 10.

FIG. 1 illustrates a perspective partial view of a room 10 in an intensive care unit. The person P, which is not illustrated here, typically lies in the bed 12 and lies flat or at an incline of his or her torso of up to 45° with respect to the plane of the bed 12. The viewing direction B can be inclined—with respect to the plane of the bed 12—from perpendicularly upward to approximately 45° with respect to the plane of the bed 12 (see FIGS. 2 and 3). The view cone thus typically scans a region that extends from the area above the bed 12 to a region in front of the bed 12.

Arranged in this region is an optical display apparatus 3, which in the present case has two display areas 4, 5, which are arranged in the viewing direction B of the person P at an angle β of between 90° and 160°, in particular at an angle of between 110° and 120°, very particularly at an angle β of 114°, with the angle β being measured from a plane E which extends above and parallel to the stationary lying person P. The transition region between the two display areas 4, 5 has a radius of curvature of 20 to 40 cm.

The optical display apparatus 3, i.e. both display areas 4, 5 are here 2.44 m wide, the total length of the two display areas 4, 5 is here in the developed view 5 m, such that the horizontal display area 4 goes beyond the head region of the person P. In principle, the size of the optical display apparatus 3 can be matched to the person P.

For the stationary lying person P, the optical display apparatus 3 substantially fills a viewing region of at least 70°, such that it is possible herewith to influence the optical senses of the person P in a targeted fashion.

In other embodiments, different measurements and angles can be selected.

The embodiment of the system for influencing the senses, however, is not only directed at optical stimuli, but in combination it also takes account of the influencing of the acoustic stimuli. Both measures together and in interaction make up the system.

To this end, a sound insulating apparatus 2 is arranged in the room 10 behind the bed 12, behind which the acoustically active appliances 1 are arranged and/or integrated therein. These are medical measurement and therapeutic devices, such as for example ventilators, infusors or dialysis machines. These machines emit acoustic signals in a broad spectrum, which influence the well-being of the person P in a negative way.

This system having the described optical and acoustic apparatuses is arranged in a room 10, wherein in particular more than one system can also be provided. These then form the room setup.

FIG. 1 shows that a sound insulating barrier 7 separates the bed 12 from another bed 12, not illustrated here, having a further person P. This will be explained in more detail below.

Also arranged in the room 10 is a light controller 6 (illustrated here only by way of example), with which the light in the room 10 can be adapted in particular to the daily rhythm, as was described above. The optical display apparatus 3 (see FIG. 4) can serve not only for the representation of optical contents but also for room illumination.

Using diagnostic devices located in room 10, the effect of the stimuli on the person P can be registered. It is thus, if appropriate, also possible to realize a feedback means in which the acoustic and optical stimuli are matched to the respective reactions in the person P.

FIG. 1A illustrates a sectional view of a room 10, in which two beds 12 are arranged on opposite sides of a sound-proofed room 20 (observation room). The room setup of the rooms 10—in particular the sound insulating apparatus 2 and the optical display apparatus 3—here corresponds to the embodiment in FIG. 1, with the result that reference can be made to the above description.

The persons P here lie in the beds 12 with their torsos at an incline (approximately 35 to 40° with respect to the plane of the bed 12), such that the viewing direction B is aimed at an observation window 11. In order to avoid irritating reflections, in particular the viewing of one's own reflected image, the panes of the observation window 11 are inclined away from the persons P by 8° with respect to the vertical. The care providers in the observation room 20 can see the persons P well even with this geometry of the observation window 11.

FIG. 1A illustrates by way of arrows that which is visible in each case for the persons P. The inclined observation windows 11 do not reflect the respective reflected image back to the person P.

By using polarization films on both observation windows 11 (in each case rotated with respect to one another by 90°), a complete view through to the observation room 20 is prevented. FIG. 1A also illustrates by way of arrows that the persons P can be seen in each case only through an observation window 11.

Figure 2:
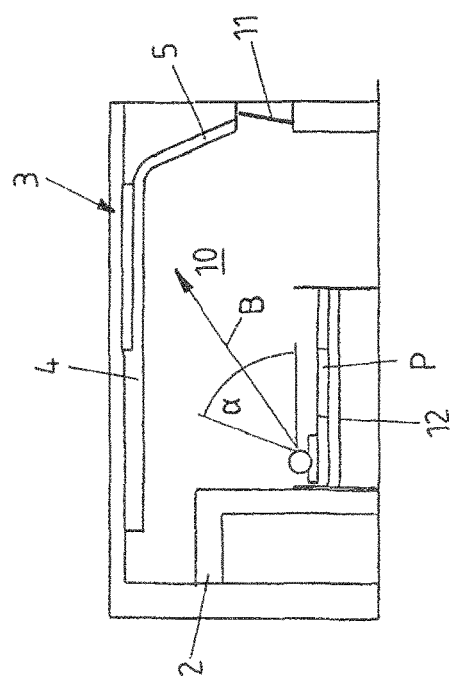
FIG. 2 shows a view of an embodiment of the system for influencing a lying person, wherein the person is lying flat.

FIG. 2 illustrates a room 10, in which a person P lies flat in a bed 12. The viewing direction B is inclined approximately by 45° with respect to the plane of the bed 12, with the result that it is incident on the first display area 4 of the optical display apparatus 3. Arranged in the horizontal first display area 4 is a first luminous means 30 (here a luminous field having LEDs), which is particularly suited and configured to adapt illumination to the time of day. This will be explained in more detail below. This first luminous means 30 as part of the optical display apparatus 3 is arranged at a view cone of 30° for the flat lying person P.

The two display areas 4, 5 of the optical display apparatus 3 are furthermore configured such that the latter is located in this location substantially completely within the field of vision of the person P. The view cone here has an opening angle of 70°, i.e. 35° above and below the viewing direction B. This illustration also shows that the optical display apparatus 3 extends backward beyond the head of the person P, such that the optical display apparatus 3 is captured even with peripheral vision.

FIG. 3 illustrates the same situation as FIG. 2, except that here the person P is inclined in the head region by 35 to 40°. The viewing direction B thus correspondingly shifts downward by 25°, such that the view cone of 70° also captures parts of the room 10 that are not covered by the optical display apparatus 3.

In alternative embodiments, the size and/or form of the optical display apparatus 3 can have a different configuration. For example, a curved area can be used instead of a plurality of planar display areas 4, 5.

FIG. 4 illustrates a sectional view of a detail of an embodiment of the optical display apparatus 3. A first luminous means 30 having LEDs provides white light, which serves as basic illumination, task lighting and biodynamic lighting. In the embodiment, an LED grid with white light LEDs having illumination intensities of up to at least 1700 lx is used, wherein warm white and cold white are switched together in alternation, which illumination intensities are infinitely variable such that, in sum, a light-temperature of 2700 to 6500 K is achieved and various scenarios with different proportions (color temperature) may be represented for the person P.

A second luminous means 31 in the form of an LED grid serves for displaying optical stimuli such as optical patterns or images on a projection area 32. The second luminous means 31 forms the projection plane for the entertainment light/the playing of visual contents and/or for an RGB color space.

The luminous means 30, 31 project onto the translucent, sound-absorbing projection area 32 (i.e. material having a low impedance), such that the person P can perceive the patterns and/or images on the projection area 32. The projection area 32 has a light transmittance of 52%.

The two luminous means 30, 31 are controllable independently of one another, such that in particular technically differing grids (LED or OLED) form light sources which are controllable, at the same time or independently of one another, in a manner in which they are offset with respect to one another or above one another. It is thus possible to integrate completely different qualities and embodiments within one setup, such that an impression of a frame-less architecturally room-forming effective surface (light-emitting ceiling and/or wall) is obtained, and not that of a technical screen.

Alternatively, OLEDs or other luminous means can be used in place of the LED.

Mounted at the periphery of the optical display apparatus 3 is here in each case an indirect illumination apparatus 8. To this end, a third luminous means 34 emits light onto an inclined reflective area 35. The inclination is oriented such that it is exactly the region of the contrast line between the ceiling and the optical display apparatus 3 that is irradiated. As a result, the peripheral region is optically concealed by using indirect ceiling illumination 8. As a result, the periphery of the optical display apparatus 3 is visually resolved for a person P, which gives a pleasant appearance for the overall viewing of the optical display apparatus 3 from the stationary position of the person P, since it reduces glare for the person P. It is possible in principle that not all sides of the optical display apparatus 3 are provided with indirect illumination 8.

Figure 4A:
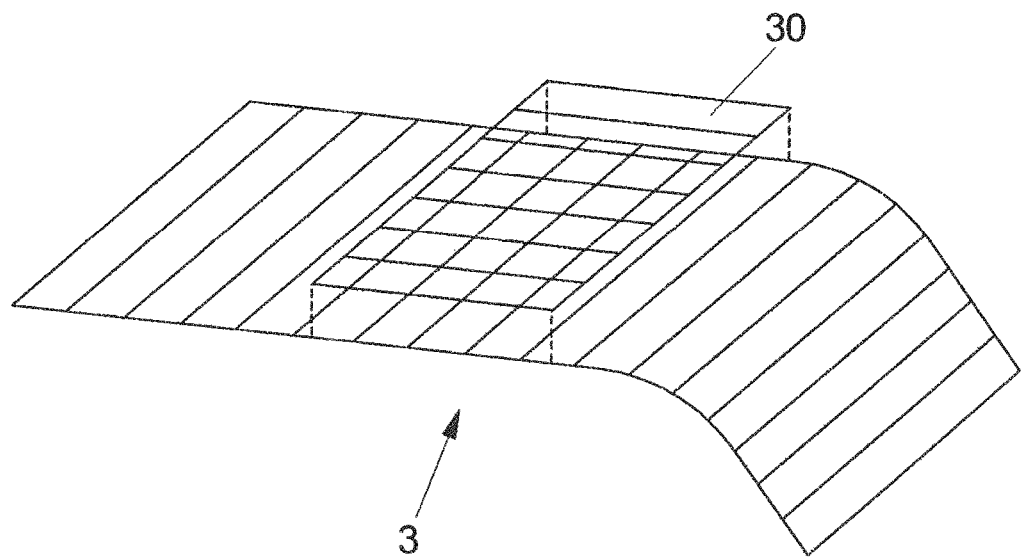
FIG. 4A shows a perspective illustration of an embodiment of an optical display apparatus.

FIG. 4A illustrates a schematically perspective view of the optical display apparatus 3. A first luminous means 30 here extends only over part of the second luminous means 31, wherein the second luminous means 31 is formed here such that ultimately the first and second display areas 3, 4 are formed.

Figure 5:
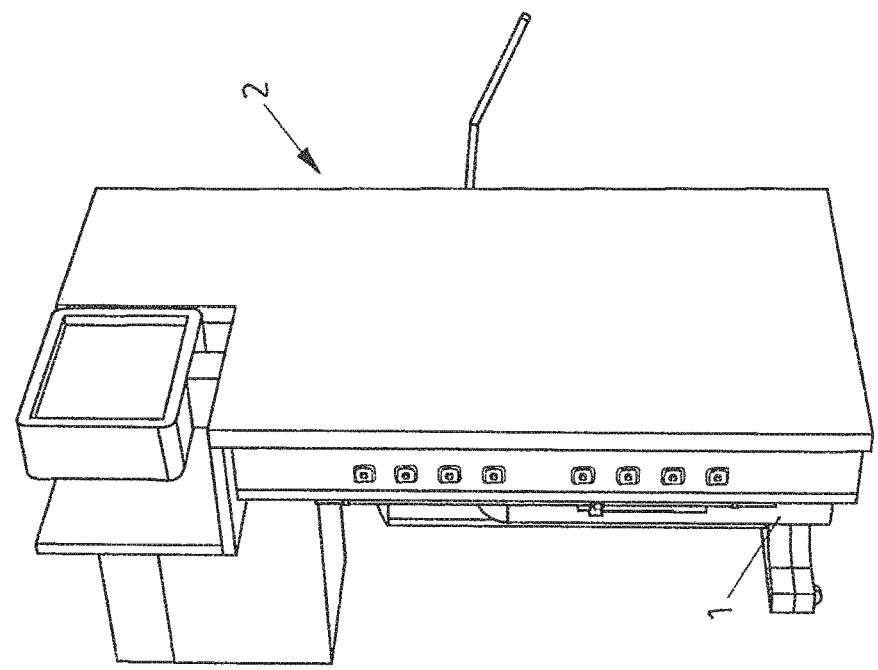
FIG. 5 shows a view of an embodiment of a sound insulating apparatus.

FIG. 5 illustrates one embodiment of a sound insulating apparatus 2, which is typically arranged at the head end of the person P (see FIG. 1). It screens off acoustically active medical devices 1 with respect to the room 10, and in particular also with respect to the person P. Arranged at the side and behind the sound insulating apparatus 2 are connections for electricity, data lines, oxygen and/or compression air. Likewise integrated in this sound insulating apparatus 2 is a monitor for physiological data (hemodynamic monitor) of the person P.

FIG. 6 illustrates an embodiment of a sound insulating barrier 7, as can be arranged for example between two persons P in a room 10. The persons P are mutually protected here against emissions. A region 9 for affixing personal objects can be arranged on the sound insulating barrier 7, which region can be perceived by the person P by way of viewing from the side. In addition, movable carriages are attached in the sound insulating barrier 7, which are necessary for example when caring or effecting therapy for the person P.

At least two openings, through which sounds can enter from the room 10, can be furthermore arranged in the sound insulating barrier 7 and/or also in the sound insulating apparatus. Damping material is arranged inside the sound insulating barrier 7 and/or the sound insulating apparatus 2, with the result that sound energy from the room is absorbed.

LIST OF REFERENCE SIGNS 1 acoustic active appliances
2 sound insulating apparatus
3 optical display apparatus
4 first display area of the optical display apparatus
5 second display area of the optical display apparatus
6 light controller
7 sound insulating barrier
8 indirect ceiling illumination
9 region for affixing personal objects
10 room
11 observation window
12 bed
20 soundproofed room (for example observation room)
30 first luminous means, luminous field
31 second luminous means, luminous field
32 covering/projection area
34 third luminous means 35 reflective area
B viewing direction
E plane
P person
α a viewing angle
β angle between two display areas of the optical display apparatus

The invention claimed is:

1. A system for influencing the senses of a person in a room for measuring and/or influencing physiological parameters of the person, when the person is substantially stationary and lying in the room during the measurement and/or influencing, comprising:
   a sound insulating apparatus for screening off acoustically active devices with respect to the person, wherein the acoustically active devices serve for measuring and/or influencing the physiological parameters in the room, and
   an optical display apparatus for offering optical stimuli and/or signals for the person in the field of view of the person, wherein the optical display apparatus is configured to extend in at least one viewing direction of the stationary lying person over a viewing angle of at least 40° and at most 180°, wherein the viewing angle extends in a plane that extends down from the viewing direction or to the left and to the right from the viewing direction, the optical display apparatus comprising:
      a first luminous field having LEDs or an OLED, for functional illumination, task lighting and/or biodynamic lighting of the room within the region of the person, and
      a second luminous field, which is controllable independently of the first luminous field, having an LED grid for displaying patterns or optical stimuli as an entertainment light or for playing visual contents,
      wherein the first and second luminous fields are arranged one above the other, wherein the optical signals of the two luminous fields are superposed and incident on a translucent projection area, which is configured to be located in a field of vision of the person.

2. The system as claimed in claim 1, wherein the sound insulating apparatus is configured to reduce the average sound emission of the active acoustic devices at the person in the room to at most 55 dB(A).

3. The system as claimed in claim 1, wherein the sound insulating apparatus has a means for absorbing and damping sound that is emitted within the sound insulating apparatus and/or directed from the room into the sound insulating apparatus.

4. The system as claimed in claim 1, wherein the optical display apparatus is configured to extend behind a head of the stationary lying person.

5. The system as claimed in claim 1, wherein the optical display apparatus has at least first and second spatially differently oriented display areas or a curved display, area, wherein the optical display apparatus is configured to be arranged at least partially above the stationary lying person in a plane that is oriented substantially parallel to the lying position of the person.

6. The system as claimed in claim 5, wherein the optical display apparatus comprises first and second spatially differently oriented display areas, wherein the second display area of the optical display apparatus is configured to be arranged in the viewing direction of the person at an angle of between 90° and 160°, wherein the angle is measured from a plane that extends above and parallel to the stationary lying person.

7. The system as in claim 6, wherein the second display area of the optical display apparatus is arranged in the viewing direction of the person at an angle of between 110° and 120°.

8. The system as in claim 6, wherein the second display area of the optical display apparatus is arranged in the viewing direction of the person at an angle of 114°.

9. The system as claimed in claim 5, wherein the optical display apparatus comprises first and second spatially differently oriented display areas, wherein a transition region between the first display area of the optical display apparatus and the second display area of the optical display apparatus has a rounded configuration having a radius of curvature of between 20 and 40 cm.

10. The system as claimed in claim 1, wherein the optical stimuli and/or signals that originate from the optical display apparatus include information representations.

11. The system as claimed in claim 1, wherein optical stimuli and/or signals are displayable for the stationary lying person using the optical display apparatus, wherein the stimuli and/or signals are preprogrammed and/or controllable by way of data measured on the person.

12. The system as in claim 1, wherein the optical display apparatus extends over a viewing angle between 55° and 75°.

13. The system as in claim 1, wherein the optical display apparatus extends over a viewing angle of 70°.

14. A room setup having a system for influencing the senses of a person in a room for measuring and/or influencing physiological parameters of the person, wherein the person is substantially stationary and lying in the room during the measurement and/or influencing, comprising:
   sound-damping materials in at least part of the floor, the walls and/or the ceiling of the room, wherein the system comprises:
   a sound insulating apparatus for screening off acoustically active devices with respect to the person, wherein the acoustically active devices serve for measuring and/or influencing the physiological parameters in the room, and
   an optical display apparatus for offering optical stimuli and/or signals for the person in the field of view of the person, wherein the optical display apparatus extends in at least one viewing direction of the stationary lying person over a viewing angle of at least 40° and at most 180°, wherein the viewing angle extends in a plane that extends down from the viewing direction or to the left and to the right from the viewing direction, the optical display apparatus comprising:
      a first luminous field having LEDs or an OLED, for functional illumination, task lighting and/or biodynamic lighting of the room within the region of the person, and
      a second luminous field, which is controllable independently of the first luminous field, having an LED grid for displaying patterns or optical stimuli as an entertainment light or for playing visual contents,
      wherein the first and second luminous fields are arranged one above the other, wherein the optical signals of the two luminous fields are superposed and incident on a translucent projection area, which is configured to be located in a field of vision of the person.

15. The room setup as claimed in claim 14, comprising at least two systems wherein in each case one sound insulating apparatus is configured to be arranged between two stationary lying persons, as a viewing protection barrier, wherein the sound insulating apparatus has at least partially a surface having a wood structure.

16. The room setup as claimed in claim 14, further comprising at least one observation window for observers outside the room, wherein the at least one observation window is inclined by 5 to 10° with respect to a wall of the room to avoid reflected images of the lying stationary person.

17. The room setup as claimed in claim 14, wherein two opposite rooms are connected via an intermediate observation room having at least two observation windows, with the result that observation of two rooms from the observation room is made possible.

18. The room setup as claimed in claim 14, comprising a light controller of the room which provides lighting having the following light parameters:

light intensity during the day: 300 lx (in the morning), 1700 lx (noon) and 100 lx (in the evening), light intensity at night: <3 lx, light color: 2700-6500 K over the course of the day matched to a natural progression, light temperature infinitely variable in different scenarios with different percentage proportions, and/or luminance <500 cd m$^{-2}$.

19. The room setup as claimed in claim 14, comprising a soundproofed room having at least one workstation for care providers that includes storage segments and/or shelving, and, an alarm station for playing acoustic alarms.

20. The room setup of claim 14, wherein the optical display apparatus extends over a viewing angle between 55° and 75°.

21. The room setup of claim 14, wherein the optical display apparatus extends over a viewing angle of 70°.

\* \* \* \* \*

UNITED STATES PATENT AND TRADEMARK OFFICE
CERTIFICATE OF CORRECTION

PATENT NO.         : 10,420,912 B2
APPLICATION NO.    : 15/500639
DATED              : September 24, 2019
INVENTOR(S)        : Alawi Lütz et al.

Page 1 of 1

It is certified that error appears in the above-identified patent and that said Letters Patent is hereby corrected as shown below:

In the Claims

Column 15, Line 58, Claim 5, delete "display," and insert -- display --

Signed and Sealed this
Twenty-fourth Day of December, 2019

Andrei Iancu
*Director of the United States Patent and Trademark Office*